United States Patent
Acton et al.

(10) Patent No.: US 8,216,547 B2
(45) Date of Patent: Jul. 10, 2012

(54) RADIOLABELLED TRP M8 RECEPTOR LIGANDS

(75) Inventors: Paul D. Acton, Hatboro, PA (US);
Dennis J. Hlasta, Doylestown, PA (US);
Jay M. Matthews, Lansdale, PA (US);
James J. McNally, Souderton, PA (US)

(73) Assignee: Janssen Pharmaceutica NV, Beerse (BE)

( * ) Notice: Subject to any disclaimer, the term of this patent is extended or adjusted under 35 U.S.C. 154(b) by 378 days.

(21) Appl. No.: 12/500,334

(22) Filed: Jul. 9, 2009

(65) Prior Publication Data

US 2010/0015053 A1 Jan. 21, 2010

Related U.S. Application Data

(60) Provisional application No. 61/081,904, filed on Jul. 18, 2008.

(51) Int. Cl.
*A61K 51/00* (2006.01)
*A61M 36/14* (2006.01)
(52) U.S. Cl. ............ 424/1.89; 424/1.11; 424/1.65; 424/1.81; 424/1.85
(58) Field of Classification Search ............ 424/1.11, 424/1.65, 1.81, 1.85, 1.89, 9.1; 549/1; 562/1, 562/400; 568/18, 700
See application file for complete search history.

(56) References Cited

FOREIGN PATENT DOCUMENTS

| WO | WO 2005/039649 | 5/2005 |
|---|---|---|
| WO | WO 2009/012430 | 1/2009 |

OTHER PUBLICATIONS

Souillac, et al (Characterization of Delivery Systems, Differential Scanning Calorimetry, pp. 217-218 in Encyclopedia of Controlled Drug Delivery, 1999, John Wiley & Sons, pp. 212-227).*
Vippagunta et al (Advanced Drug Delivery Reviews, 2001, vol. 48, pp. 3-26).*
David D. McKemy et al., "Identification of a cold receptor reveals a general role for TRP channels in thermosensation", Nature, Mar. 2002, pp. 52-58, vol. 416, Macmillan Magazines Ltd.
Junji Abe et al., "$Ca^{2+}$-dependent PKC activation mediates menthol-induced desensitization of transient receptor potential M8", Neuroscience Letters, 2006, pp. 140-144, vol. 397, Elsevier Ireland Ltd.
Louis S. Premkumar et al., "Downregulation of Transient Receptor Potential Melastatin 8 by Protein Kinase C-Mediated Dephosphorylation", The Journal of Neuroscience, Dec. 7, 2005, pp. 11322-11329, vol. 25(49), Society of Neuroscience.
Kimiko Kobayashi et al., "Distinct Expression of TRPM8, TRPA1, and TRPV1 mRNAs in Rat Primary Afferent Neurons with Aδ/C-Fibers and Colocalization with Trk Receptors", The Journal of Comparative Neurology, 2005, pp. 596-606, vol. 493(4), Wiley-Liss, Inc.
Carolina Roza et al., "Cold sensitivity in axotomized fibers of experimental neuromas in mice", Pain, 2006, pp. 24-35, vol. 120(1-2), Elsevier B.V.
Hong Xing et al., "Chemical and Cold Sensitivity of Two Distinct Populations of TRPM8-Expressing Somatosensory Neurons", J. Neurophysiol, Feb. 2006, pp. 1221-1230, vol. 95(2), The American Physiological Society.
Beck et al., "Prospects for prostate cancer imaging and therapy using high-affinity TRPM8 activators", Cell Calcium, vol. 41, No. 3, (2007), pp. 285-294.
International Search Report for corresponding Application No. PCT/US2009/050675 mailed Apr. 6, 2010.

* cited by examiner

*Primary Examiner* — D L Jones

(57) ABSTRACT

The present invention is directed to radiolabelled ligands, useful for the labeling and imaging of TRP M8 (transient receptor potential M8 channel) functionality. The present invention is further directed to pharmaceutical compositions comprising the radiolabelled ligands and methods for the preparation of the radiolabelled ligands.

23 Claims, No Drawings

RADIOLABELLED TRP M8 RECEPTOR LIGANDS

CROSS REFERENCE TO RELATED APPLICATIONS

This application claims the benefit of U.S. Provisional Application 61/081,904, filed on Jul. 18, 2008, which is incorporated by reference herein in its entirety.

FIELD OF THE INVENTION

The present invention is directed to radiolabelled ligands, useful for the labeling and imaging of TRP M8 (transient receptor potential M8 channel) functionality. The present invention is further directed to pharmaceutical compositions comprising the radiolabelled ligands and methods for the preparation of the radiolabelled ligands.

BACKGROUND OF THE INVENTION

Transient receptor potential (TRP) channels are non-selective cation channels that are activated by a variety of stimuli. Numerous members of the ion channel family have been identified to date, including the cold-menthol receptor, also called TRP M8 (McKemy, D. D., et. al., *Nature* 2002, 416 (6876), 52-58). Collectively, the TRP channels and related TRP-like receptors connote sensory responsivity to the entire continuum of thermal exposure, selectively responding to threshold temperatures ranging from noxious hot through noxious cold as well as to certain chemicals that mimic these sensations. Specifically, TRP M8 is known to be stimulated by cool to cold temperatures as well as by chemical agents such as menthol and icilin, which may be responsible for the therapeutic cooling sensation that these agents provoke.

TRP M8 is located on primary nociceptive neurons (A-delta and C-fibers) and is also modulated by inflammation-mediated second messenger signals (Abe, J., et al., *Neurosci Lett* 2006, 397(1-2), 140-144; Premkumar, L. S., et al., *J. Neurosci*, 2005, 25(49), 11322-11329). The localization of TRPM8 on both A-delta and C-fibers may provide a basis for abnormal cold sensitivity in pathologic conditions wherein these neurons are altered, resulting in pain, often of a burning nature (Kobayashi, K., et al., *J Comp Neurol*, 2005, 493(4), 596-606; Roza, C., et al., *Pain*, 2006, 120(1-2), 24-35; and Xing, H., et al., *J Neurophysiol*, 2006, 95(2), 1221-30). Cold intolerance and paradoxical burning sensations induced by chemical or thermal cooling closely parallel symptoms seen in a wide range of clinical disorders and thus provide a strong rationale for the development of TRP M8 modulators as novel antihyperalgesic or antiallodynic agents. TRP M8 is also known to be expressed in the brain, lung, bladder, gastrointestinal tract, blood vessels, prostate and immune cells, thereby providing the possibility for therapeutic modulation in a wide range of maladies.

Non-invasive nuclear imaging techniques can be used to obtain basic and diagnostic information about the physiology and biochemistry of living subjects, including experimental animals, humans and patients. These techniques rely on the use of imaging instruments that can detect radiation emitted from radiotracers administered to the living subjects. The information obtained can be reconstructed to provide planar and tomographic images which reveal the distribution and/or concentration of the radiotracer as a function of time.

Positron emission tomography (PET) is a non-invasive imaging technique that offers the highest spatial and temporal resolution of all the nuclear medicine imaging modalities and has the added advantage that it can allow for true quantitation of tracer concentration in tissues. The technique involves the use of radiotracers, labeled with positron emitting radionuclides. Radiotracers are designed to have in vivo properties which permit measurement of parameters regarding the physiology or biochemistry of a variety of processes in living tissue.

Compounds can be labeled with positron or gamma emitting radionuclides. The most commonly used positron emitting radionuclides are $^{15}O$, $^{13}N$, $^{11}C$ and $^{18}F$, which are accelerator produced and have half lives of 2, 10, 20 and 110 minutes, respectively. The most widely used gamma emitting radionuclides are $^{99m}Tc$, $^{201}Tl$ and $^{123}I$.

There remains a need for radiolabelled ligands which bind to the TRP M8 receptor in the central and/or peripheral nervous system, for example in brain and/or spinal cord, of a subject.

SUMMARY OF THE INVENTION

The present invention is directed to a radiolabelled compound of formula (A)

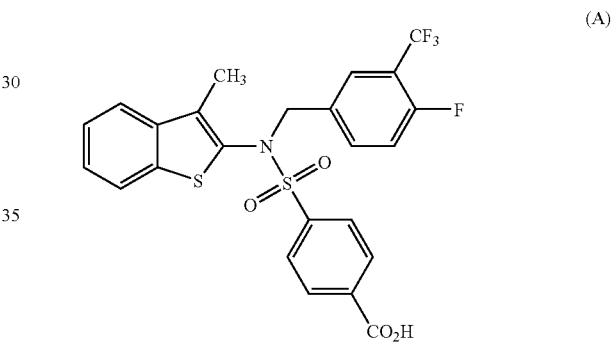

or solvate, or pharmaceutically acceptable salt thereof; wherein one or more of the C and/or F atoms on the compound of formula (A) is replaced with the corresponding $^{11}C$ or $^{18}F$.

The present invention is further directed to a radiolabelled compound of formula (B)

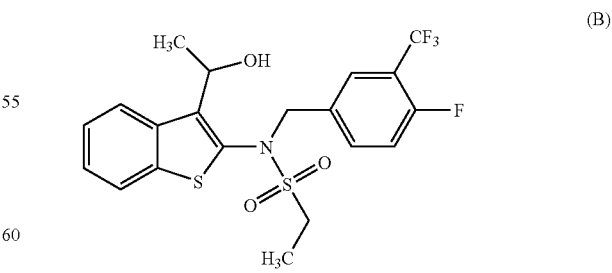

or solvate, or pharmaceutically acceptable salt thereof; wherein one or more of the C and/or F atoms on the compound of formula (B) is replaced with the corresponding $^{11}C$ or $^{18}F$.

The present invention is further directed to a radiolabelled compound of formula (I)

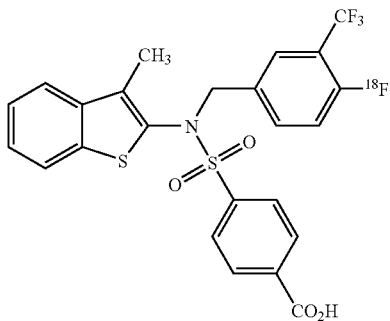

(I)

or solvate, or pharmaceutically acceptable salt thereof.

The present invention is further directed to radiolabelled compounds of formula (II)

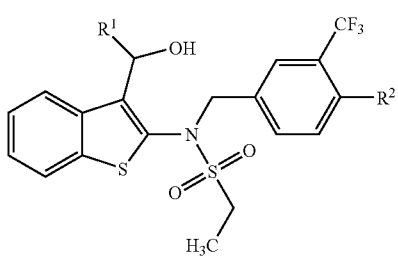

(II)

wherein $R^1$ is $CH_3$ and $R^2$ is $^{18}F$;
alternatively, $R^1$ is $^{11}CH_3$ and $R^2$ is F;
or a solvate or pharmaceutically acceptable salt thereof.

The present invention is further directed to processes for the preparation of the compounds of formula (A) and the compounds of formula (B). The present invention is further directed to processes for the preparation of the compounds of formula (I), as described in more detail herein. The present invention is further directed to processes for the preparation of the compounds of formula (II), as described in more detail herein. The present invention is further directed to a product prepared according to any of the processes described herein.

The present invention is further directed to a pharmaceutical composition comprising any of the radiolabelled compounds described herein and a pharmaceutically acceptable carrier. Preferably, the pharmaceutical composition is a liquid pharmaceutical composition.

The present invention is further directed to the use of any of the radiolabelled compounds as described herein in positron emission tomography (PET) imaging. The present invention is further directed to a method for labeling TRP M8 receptors in a subject comprising administering to a subject in need of such labeling an effective amount of any of the radiolabelled compounds described herein. The present invention is further directed to a method for imaging of TRP M8 receptors in a subject comprising comprises administering to a subject in need of such imaging an effective amount of any of the radiolabelled compounds described herein. The present invention is further directed to a method for imaging of tissues bearing TRP M8 receptors in a subject comprising administering to a subject in need of such imaging an effective amount of any of the radiolabelled compounds described herein. The present invention is also directed to a method for imaging of the central and/or peripheral nervous system (including but not limited to the brain and/or spinal cord) which comprises administering to a subject in need of such imaging an effective amount of any of the radiolabelled compounds described herein.

The present invention is further directed to a method for the detection or quantification of TRP M8 receptors in mammalian tissue comprising administering to a mammal in which such quantification is desired an effective amount of any of the radiolabelled compounds described herein. The present invention is further directed to a method for visualizing changes in TRP M8 functionality in a subject, comprising administering to a subject an effective amount of any of the radiolabelled compounds described herein. The present invention is further directed to methods for visualizing changes in TRP M8 functionality as a means of identifying new therapeutic drug indications for a TRP M8 antagonist or agonist. The present invention is further directed to a method for measuring pharmacokinetics and/or bio-distribution of a TRP M8 antagonist or agonist in an animal, preferably a human.

One skilled in the art will recognize that certain diseases and/or conditions modulated by the TRP M8 receptor, such as hyperalgesia, and the like, may be a reflection of, or caused by, an up-regulation of the TRP M8 receptor. The present invention is further directed to methods for monitoring the modulation of the TRP M8 receptor comprising administering to a patient in need thereof an effective amount of any off radiolabelled compounds described herein. The present invention is further directed to a method for monitoring the modulation of the TRP M8 receptor as a diagnostic tool for selecting patients that require and/or may respond to TRP M8 antagonist therapy comprising administering to a patient in need thereof an effective amount of any of the radiolabelled compounds described herein.

The present invention is further directed to methods of radiotherapy, wherein an intense, localized deposition of ionizing radiation is administered at the site of TRP M8 receptor concentration to ameliorate painful symptoms associated with a disease or condition modulated by the TRP M8 receptor, for example hyperalgesia, and the like The present invention is therefore directed to a method of radiotherapy comprising administering to a subject in need thereof an effective dose of any of the radiolabelled compounds described herein.

DETAILED DESCRIPTION OF THE INVENTION

The present invention is directed to radiolabelled compounds of formula (A)

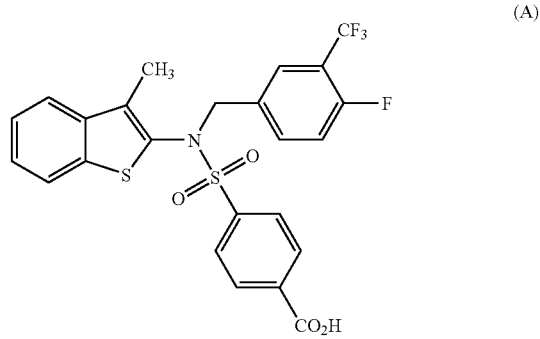

(A)

and solvates and pharmaceutically acceptable salts thereof; and further to radiolabelled compounds of formula (B)

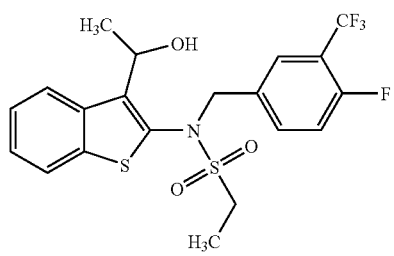

and solvates and pharmaceutically acceptable salt thereof; wherein one or more of the C and/or F atoms on the compound of formula (A) or the compound of (B) is replaced with the corresponding $^{11}$C or $^{18}$F. In an embodiment of the present invention, the carbon atom of the methyl group bound at the 3-position of the benzothienyl group on the compound of formula (A) is replaced with $^{11}$C. In another embodiment of the present invention, the carbon atom of the carboxy group, bound at the 4-position of the phenyl-sulfonyl-group on the compound of formula (A) is replaced with $^{11}$C. In another embodiment of the present invention, the terminal carbon atom on the ethylsulfonyl-portion of the compound of formula (B) is replaced with $^{11}$C.

In an embodiment of the present invention, the fluoro atom (s) of the trifluoromethyl substituent on the (3-trifluoromethyl-4-fluoro-benzyl)-portion of the compound of formula (A) or the compound of formula (B) are not radiolabelled.

The compounds of formula (A) and the compounds of formula (B) are useful in imaging TRP M8 receptor occupancy in the central and/or peripheral nervous system of a subject.

The present invention is further directed to a radiolabelled compound of formula (I)

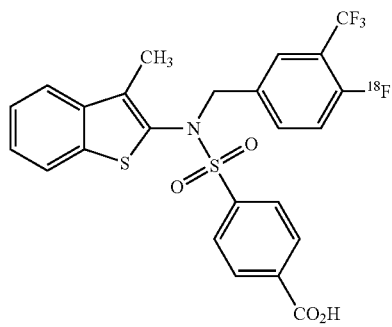

and solvates and pharmaceutically acceptable salts thereof; and further to radiolabelled compounds of formula (II)

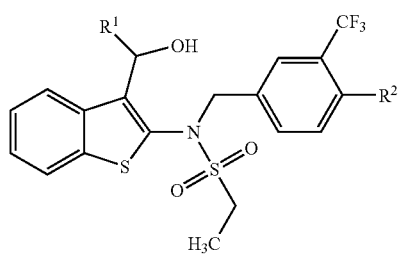

wherein $R^1$ and $R^2$ are as herein defined, and solvates and pharmaceutically acceptable salts thereof. The compound of formula (I) and the compounds of formula (II) are useful in imaging TRP M8 receptor occupancy in the central and/or peripheral nervous system of a subject.

In an embodiment, the compounds of the present invention as useful in imaging of TRP M8 occupancy in the central nervous system, more preferably in the brain and/or spinal cord. In another embodiment, the compounds of the present invention are useful in imaging TRP M8 occupancy in the peripheral nervous system.

In another embodiment, the compounds of the present invention are useful in determining the pharmacokinetics and/or bio-distribution of a compound of formula (I) and/or a compound of formula (II) in an animal, preferably a human. In another embodiment, the compounds of the present invention are useful in determining the bio-distribution of a compound of formula (I) or a compound of formula (II) in the brain, kidney, liver, heart or other organ of an animal, preferably a human.

In an embodiment of the present invention, the subject is a mammal. In another embodiment of the present invention, the subject is a human. In yet another embodiment of the present invention, the subject is a human, wherein the human has exhibited or experienced at least one symptom of disease or condition modulated by the TRP M8 receptor.

In an embodiment, the present invention is directed to a radiolabelled compound of formula (II-A)

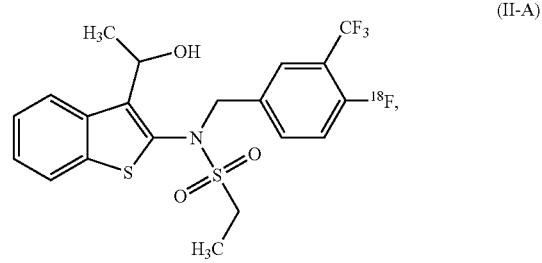

or solvate or pharmaceutically acceptable salt thereof. In another embodiment, the present invention is directed to a compound of formula (II-B)

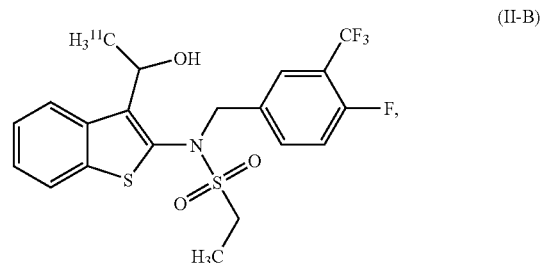

or solvate or pharmaceutically acceptable salt thereof.

The radiolabelled compounds of formula (A), formula (B), formula (I) and formula (II), as well as the corresponding non-radiolabelled compounds, are useful for treating or ameliorating a TRPM8-modulated disorder in a subject, including a mammal and/or human in which the disease, syndrome, or condition is affected by the modulation of TRPM8 receptors, such as pain, and diseases that lead to such pain, and pulmonary or vascular dysfunction.

In an embodiment, the radiolabelled compounds of formula (I) and formula (II), as well as the corresponding non-radiolabelled compounds of formula (I) and formula (II), are useful for treating or ameliorating a TRP M8-modulated disorder in a subject, including a mammal and/or human in which the disease, syndrome, or condition is affected by the modulation of TRP M8 receptors, such as pain, and diseases that lead to such pain, and pulmonary or vascular dysfunction. In particular, the compounds are useful for treating or ameliorating a TRP M8 receptor-modulated disorder including, but not limited to inflammatory pain (including, but not limited to, inflammatory hyperalgesia and inflammatory hypersensitivity), neuropathic pain, cold-intolerance or cold allodynia, peripheral vascular pain, itch, urinary incontinence, chronic obstructive pulmonary disease, pulmonary hypertension and anxiety, and other stress-related disorders.

Examples of inflammatory pain include pain due to a disease, condition, syndrome, disorder, or a pain state including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, sinus headache, tension headache, or arachnoiditis.

One type of inflammatory pain is inflammatory hyperalgesia, which can be further distinguished as inflammatory somatic hyperalgesia or inflammatory visceral hyperalgesia. Inflammatory somatic hyperalgesia can be characterized by the presence of an inflammatory hyperalgesic state in which a hypersensitivity to thermal, mechanical and/or chemical stimuli exists. Inflammatory visceral hyperalgesia can also be characterized by the presence of an inflammatory hyperalgesic state, in which an enhanced visceral irritability exists.

Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases including Crohn's Disease or ulcerative colitis.

Examples of an inflammatory hypersensitivity condition include urinary incontinence, benign prostatic hypertrophy, cough, asthma, rhinitis and nasal hypersensitivity, itch, contact dermatitis and/or dermal allergy, and chronic obstructive pulmonary disease.

Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, neuralgias (trigeminal neuralgia, glossopharyngeal neuralgia, postherpetic neuralgia and causalgia), lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

Examples of anxiety include social anxiety, post traumatic stress disorder, phobias, social phobia, special phobias, panic disorder, obsessive compulsive disorder, acute stress, disorder, separation anxiety disorder, and generalized anxiety disorder. Examples of depression include major depression, bipolar disorder, seasonal affective disorder, post natal depression, manic depression, and bipolar depression.

Radiolabelled TRP M8 ligands, when labeled with an appropriate radionuclide, are potentially useful for diagnostic imaging (for example PET imaging), basic research, and radiotherapeutic applications. Specific examples of possible imaging (including, but not limited to, investigational, diagnostic, therapeutic, prophylactic imaging) and radiotherapeutic applications, include determining the location, the relative activity and/or the abundance of TRP M8 receptors, biodistribution of TRPM8 ligand in various organs and tissues, and autoradiography to determine the distribution of TRP M8 receptors in a mammal or an organ or tissue sample thereof.

In particular, the instant radiolabelled TRP M8 receptor ligands when labeled with the positron emitting radionuclide, $^{18}F$, are useful for positron emission tomographic (PET) imaging of TRP M8 receptors within the central and peripheral nervous system of living humans and experimental animals. The radiolabelled TRP M8 receptor ligands of the present invention may further may be used as research tools to study the interaction of unlabeled TRP M8 antagonist with TRP M8 receptors in vivo via competition between the labeled drug and the radiolabelled compound for binding to the receptor. This type of study is useful for determining the relationship between TRP M8 receptor occupancy and dose of unlabeled TRP M8 receptor antagonist, as well as for studying the duration of blockade of the receptor by various doses of the unlabeled TRP M8 receptor antagonist. As a clinical tool, the radiolabelled TRP M8 receptor ligands may be used to help define a clinically efficacious dose of a TRP M8 receptor antagonist. In animal experiments, the radiolabelled TRP M8 receptor ligands can be used to provide information that is useful for choosing between potential drug candidate for selection for clinical development. The radiolabelled TRP M8 receptor ligands may also be used to study the regional distribution and concentration of TRP M8 receptors in the living human brain, as well as the brain of living experimental animals and in other organs or tissue samples.

The radiolabelled TRP M8 receptor ligands may also be used to study disease or pharmacologically related changes in TRP M8 receptor concentrations. For example, positron emission tomography (PET) tracers such as the present radiolabelled TRP M8 receptor ligands which can be used with currently available PET technology to obtain the following information: relationship between level of receptor occupancy by candidate TRP M8 antagonist and clinical efficacy in patients; dose selection for clinical trials of TRP M8 antagonists prior to initiation of long term clinical studies; comparative potencies of structurally novel TRP M8 antagonists; investigating the influence of TRP M8 antagonists on in vivo receptor affinity and density during the treatment of clinical targets with TRP M8 receptor antagonists and other agents; changes in the density and distribution of TRP M8 receptors in various diseases, syndromes, and disorders, including, but not limited to those that cause inflammatory or neuropathic pain, cold intolerance or cold allodynia, peripheral vascular pain, itch, urinary incontinence, chronic obstructive pulmonary disease (COPD), pulmonary hypertension and anxiety, and other stress-related disorders, during effective and ineffective treatment with a TRPM8 antagonist; and changes in TRP M8 receptor expression and distribution in these disorders.

In another example, the radiolabelled TRP M8 receptor ligands of the present invention may be used in PET imaging in animals (preferably mammals, more preferably humans) to determine the pharmacokinetics and/or bio-distribution of a test compound (drug). In an example, a radiolabelled TRP M8 receptor ligand of the present invention may be used in PET imaging for determining bio-distribution and/or pharmacokinetics, as follows.

A rat is anesthetized (1.5% isoflurane in oxygen), positioned in the PET camera, and the tail vein cannulated for ease of injection. An arterial or venous catheter is placed for blood sampling. About 1 mCi of a radiolabelled TRP M8 receptor ligand (preferably a radiolablelled TRP M8 receptor ligand of the present invention) is injected via its tail vein, and arterial or venous blood samples are withdrawn periodically to capture the full time-activity curve. Acquisition of images of the central and/or peripheral nervous system, and also the whole body of the animal, are started as the radiotracer is injected and continued for up to 2 hr. Regions of interest (ROIs) are drawn on the summed image, including the brain and other organs, then used to analyze the count rates in the dynamic images. Blood samples are spun in a centrifuge to separate plasma and counted in a well counter. Counts in organs, including brain, liver, kidneys, heart, etc, may be used to determine the exposure of the drug in each tissue, and further to determine the pharmacokinetics in each organ.

For the use of the instant compounds as exploratory or imaging agents the radiolabelled compounds may be administered to mammals, preferably humans, in a pharmaceutical composition, either alone or, preferably, in combination with pharmaceutically acceptable carriers or diluents, optionally with known adjuvants, such as alum, in a pharmaceutical composition, according to standard pharmaceutical practice. Such compositions can be administered orally or parenterally, including the intravenous, intramuscular, intraperitoneal, subcutaneous, rectal and topical routes of administration. Preferably, administration is intravenous. Radiotracers labeled with short-lived, positron emitting radionuclides are almost always administered via intravenous injection within less than one hour of their synthesis. This is necessary because of the short half-life of the radionuclides involved (20 and 110 minutes for $^{11}$C and $^{18}$F, respectively).

It will be appreciated that the amount of the TRP M8 receptor ligand required for use in the present invention will vary not only with the particular compounds or compositions selected but also with the route of administration, the nature of the condition being treated or studied, and the age and condition of the patient, and will ultimately be at the discretion of the patient's physician or pharmacist. When a radiolabelled TRP M8 receptor ligand according to the present invention is administered into a human subject, the amount required for imaging will normally be determined by the prescribing physician with the dosage generally varying according to the age, weight, and response of the individual patient, as well as the quantity of emission from the radionuclide.

In an embodiment, the radiolabelled TRP M8 ligands of the present invention may be administered i.v. in saline, optionally in a mixture with less than or equal to about 10% ethanol (for example, in a mixture with about 5% to about 10% ethanol). One skilled in the art will recognize that the ethanol may be used to help dissolve the radiolabelled TRP M8 ligand.

In an embodiment of the present invention, the radiolabelled TRP M8 ligands are formulated for administration in rats, at a volume of less than or equal to about 2 ml, with a total activity of about 1 mCi. In another embodiment of the present invention, the radiolabelled TRP M8 ligands are formulated for administration in humans, at a volume of about 1 mL to about 10 mL, or any range therein, for example at about 5 mL, with an injected dose resulting an a total activity in the range of from about 1 mCi to about 20 mCi, or any range therein, for example with a total activity in the range of from about 10 mCi to about 20 mCi or any range therein.

The following illustrate examples of methods of use of the radiolabelled compounds of the present invention in PET imaging.

In an example, the radiolabelled compounds of the present invention are used in PET imaging studies of patients (preferably human patients) in the clinic, according to the following procedure. A patient is pre-medicated with unlabeled TRP M8 receptor antagonist (for example, doses of approximately 30 mg/kg/day) for 2 weeks prior to the day of the experiment. A 20 G two inch venous catheter is inserted into the ulnar vein for administration the radiolabelled TRP M8 ligand, and a similar catheter inserted into a contralateral radial artery for blood sampling. The radiolabelled TRP M8 receptor ligand (<20 mCi) is administered as a bolus via i.v. catheter, and arterial blood samples are withdrawn. Blood samples are spun in a centrifuge to separate plasma and counted in a well counter, while some samples taken for further analysis of radiolabeled metabolites by HPLC. The patient is positioned in a PET camera and images of the central and/or peripheral nervous system are collected immediately after administration of the radiotracer.

In another example, the radiolabelled compounds of the present invention are used in MicroPET imaging in mammals, for example in rats, according to the following procedure. A rat is anesthetized (1.5% isoflurane in oxygen), positioned in the PET camera, and the tail vein cannulated for ease of injection. An arterial catheter may additional be placed for blood sampling. The rat is pre-injected with an unlabeled TRP M8 receptor antagonist at 60-120 min prior to injection of the radiolabelled TRP M8 ligand to measure receptor occupancy. About 1 mCi of a radiolabelled TRP M8 receptor ligand is injected via its tail vein, and arterial blood samples withdrawn periodically to capture the full time-activity curve. Acquisition of images of the central and/or peripheral nervous system is started as the radiotracer is injected and continued for up to 2 hr. Regions of interest (ROIs) are drawn on the summed image which includes the brain, then used to analyze the count rates in the dynamic images. Blood samples will be spun in a centrifuge to separate plasma and counted in a well counter, and some samples taken for further analysis of radiolabeled metabolites using HPLC.

In yet another example, the radiolabelled compounds of the present invention are used in PET imaging in mammals, for example in dogs, according to the following procedure. Female beagle dogs weighing 7.7-14.6 kg are pre-medicated with unlabeled TRP M8 receptor antagonist (for example, at doses of 30 mg/kg/day) for 2 weeks prior to the day of the experiment. A 20 G two inch venous catheter is placed into the right front leg ulnar vein through which anesthesia is introduced by sodium pentobarbital 25-30 mg/kg in 3-4 ml and maintained with additional pentobarbital at an average dose of 3 mg/kg/hr. Another catheter is inserted into the contralateral ulnar vein for administration of the radiolabelled TRP M8 ligand. An arterial catheter may be placed for blood sampling. Oxygen saturation of circulating blood is measured with a pulse oximeter (Nellcor Inc., Hayward, Calif.) placed on the tongue of the animal. Circulatory volume is maintained by intravenous infusion of isotonic saline. A 22 G cannula is inserted into the anterior tibial or distal femoral artery for continuous pressure monitoring. EKG, heart rate, and core temperature are monitored continuously. In particular, EKG is observed for 20 ST segment changes and arrhythmias. The animal is positioned in the PET camera and a dose of radiolabelled TRP M8 receptor ligand (<20 mCi) is administered via i.v. catheter. Images are acquired for up to 2 hrs followed administration of the radiolabelled TRP M8 ligand. Within ten minutes of the injection of the radiolabelled TRP M8 ligand, and at the end of the imaging session, 1 ml blood samples are obtained for determining the plasma concentration of the test compound. At the conclusion of the study, animals are recovered and returned to special animal housing until they are no longer radioactive.

Following PET imaging, the acquired images may be analyzed as follows. For determining the distribution of radiotracer, regions of interest (ROIs) in the central (e.g. brain, spinal cord, etc.) and/or peripheral nervous system are drawn on the reconstructed images. These regions are used to generate time activity curves, which are combined with metabolite-corrected arterial plasma count data using a compartmental tracer kinetic model. The outcome measures include quantitative parameters associated with radiolabelled TRP M8 ligand binding, including distribution volumes and binding potentials. In the presence of cold TRP M8 receptor antagonists, the change in these parameters can be calculated as a function of dose, providing a measure of the occupancy of the receptor by the cold antagonist. These results can further provide $ED_{50}$, or the effective dose required to block 50% of the available TRP M8 receptors.

Abbreviations used in the specification, particularly the Schemes and Examples, which follow herein, are as follows:

| | |
|---|---|
| AsPh₃ = | Triphenylarsine |
| DCM = | Dichloromethane |
| DEAD = | Diethylazodicarboxylate |
| DMF = | N,N-Dimethylformamide |
| DMSO = | Dimethylsulfoxide |
| EtOAc = | Ethyl acetate |
| HPLC = | High Pressure Liquid Chromatography |

-continued

| | |
|---|---|
| IPA = | Isopropyl alcohol |
| MeOH = | Methanol |
| NaOMe = | Sodium methoxide |
| Ph₃PI₂ = | Triphenylphosphine diiodide |
| Ph₃PBr₂ = | Triphenylphosphine dibromide |
| Pd₂(dba)₃ = | Tris(dibenzylidene acetone)dipalladium(0) |
| PET = | Positron emission tomography |
| Ph = | Phenyl |
| THF = | Tetrahydrofuran |
| TRP M8 = | Transient receptor potential M8 channel |

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "crown ether" shall denote a heterocyclic compound consisting of a ring containing several ether groups, for example rings comprising repeating units of ethylene oxide, including but not limited to the corresponding tetramer, pentamer and hexamer. Unless otherwise noted, the first number in a crown ether's name refers to the number of atoms in the cycle, and the second number refers to the number of those atoms which are oxygen. Suitable examples of crown ethers include, but are not limited to 12-crown-4, 15-crown-5, 18-crown-6, dibenzo-18-crown-6, diaza-18-crown-6, and the like, preferably 18-crown-6.

As used herein, unless otherwise noted, the term "cryptand" shall mean any macropolycyclic polyazo-polyether, where the three-coordinate nitrogen atoms provide the vertices of a three-dimensional structure. Suitable examples include, but are not limited to N[CH$_2$CH$_2$OCH$_2$CH$_2$OCH$_2$CH$_2$]$_3$N (also known as 1,10-diaza-4,7,13,16,21,24-hexaoxabicyclo[8.8.8]hexacosane), KRYPTOFIX® 2.2.2 (available from VWR Scientific, Aldrich and Fluka), and the like.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[(Rmoles−Smoles)/(Rmoles+Smoles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

ee=([α−obs]/[α−max])×100.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The radiolabelled compounds of formula (A) and formula (B) may be prepared by replacing the non-radioactive C and/or F atoms with the corresponding $^{11}$C and $^{18}$F atoms.

The TRP M8 receptor ligands of the present invention, which incorporate a radionuclide, may be prepared as described in the Schemes which follow herein. The compound of formula (I) may be prepared according to the process outline in Scheme 1.

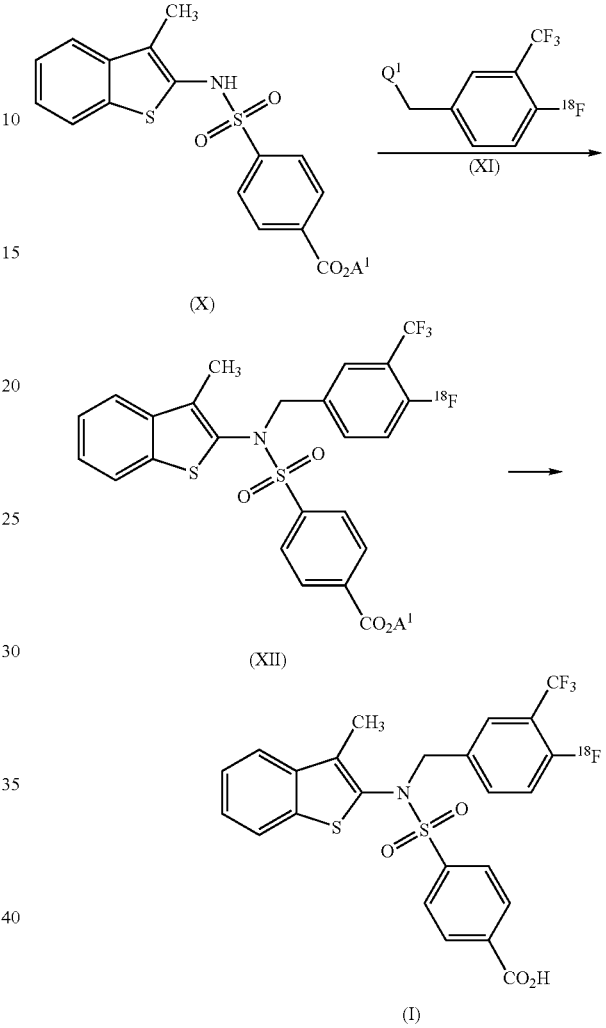

Accordingly, a suitably substituted compound of formula (X), wherein A$^1$ is C$_{1-4}$alkyl, preferably methyl, a known compound or compound prepared by known methods, is reacted with a suitably substituted radiolabelled compound of formula (XI), wherein Q$^1$ is a suitably selected leaving group, to yield the corresponding compound of formula (XII).

For example, wherein Q$^1$ is a leaving group such as Br, Cl, I, and the like, preferably Br, the compound of formula (X) is reacted with the compound of formula (XI), wherein the compound of formula (XI) is reacted with compound of formula (X); wherein the compound of formula (X) is present in a molar excess; in the presence of an inorganic base such as NaH, Cs$_2$CO$_3$, K$_2$CO$_3$, and the like, preferably NaH; in an organic solvent such as DMF, THF, 1,4-dioxane, DMSO, and the like; preferably at a temperature in the range of from about 25° C. to about 100° C.; to yield the corresponding compound of formula (XII).

Alternatively, wherein the compound of formula (XI), Q1 is a leaving group such as OH, the compound of formula (X) is reacted with the compound of formula (XI), under Mitsunobu conditions (in the presence of triphenylphosphine, and the like, in the presence of a coupling agent such as DEAD, and the like, in an organic solvent such as THF, and the like), to yield the corresponding compound of formula (XII).

The compound of formula (XII) is reacted with a suitably selected base such as NaOH, LiOH, and the like, preferably NaOH; in an organic solvent or mixture of organic solvent and water such as methanol, ethanol, methanol/water, and the like; to yield the corresponding compound of formula (I).

The compound of formula (I) may alternatively be prepared according to the process outlined in Scheme 2, below.

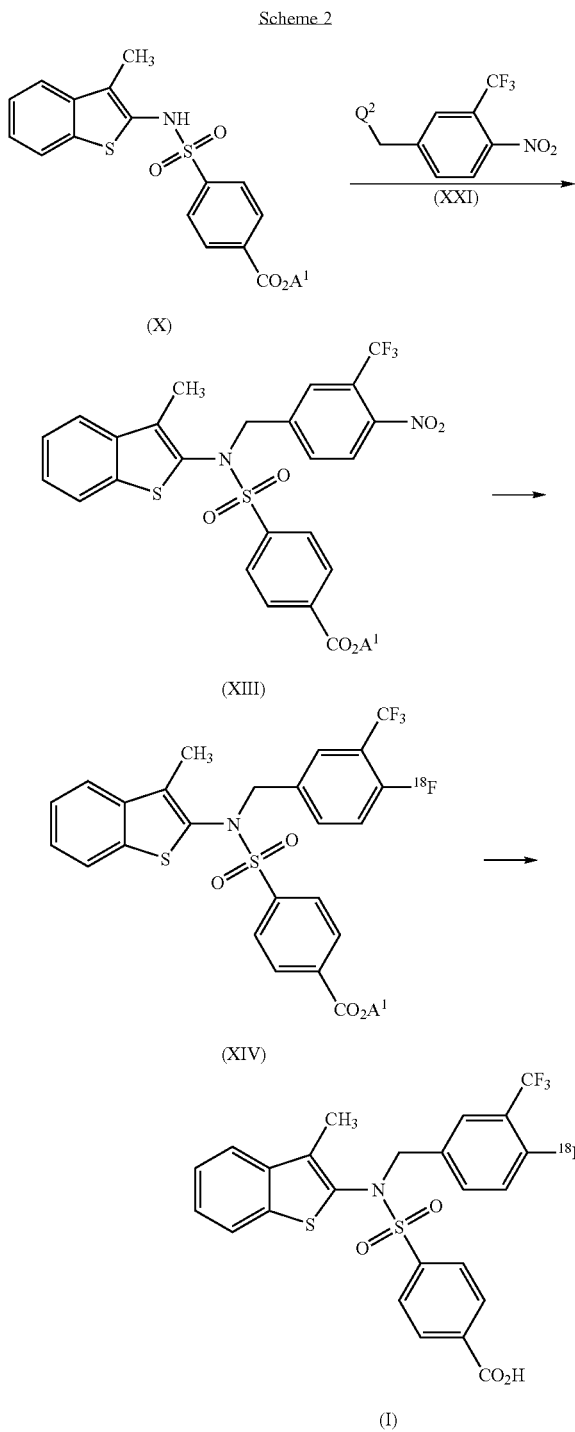

reacted with a suitably substituted radiolabelled compound of formula (XXI), wherein $Q^2$ is a suitably selected leaving group such as Br, Cl, I and the like, preferably Br; wherein the compound of formula (X) is present in a molar excess; in the presence of an inorganic base such as NaH, $Cs_2CO_3$, $K_2CO_3$, and the like, preferably NaH; in an organic solvent such as DMF, THF, 1,4-dioxane, DMSO, and the like; preferably at a temperature in the range of from about 25° C. to about 100° C.; to yield the corresponding compound of formula (XIII).

The compound of formula (XIII) is reacted with radiolabelled $^{18}F^-$, a known compound or compound prepared by known methods; in the presence of crown ether such as 18-crown-6, and the like or a cryptand such as KRYPTOFIX® 2.2.2, and the like; wherein the compound of formula (XIII) is preferably present in a molar excess of greater than about 100 times; in an organic solvent such as DMSO, DMF, $CH_3CN$, and the like, preferably DMSO; to yield the corresponding radiolabelled compound of formula (XIV).

The compound of formula (XIV) is reacted with a suitably selected base such as NaOH, LiOH, and the like, preferably NaOH; in an organic solvent or mixture of organic solvent and water such as methanol, ethanol, methanol/water, and the like; to yield the corresponding compound of formula (I).

The compound of formula (II-A) may be prepared according to the process outlined in Scheme 3.

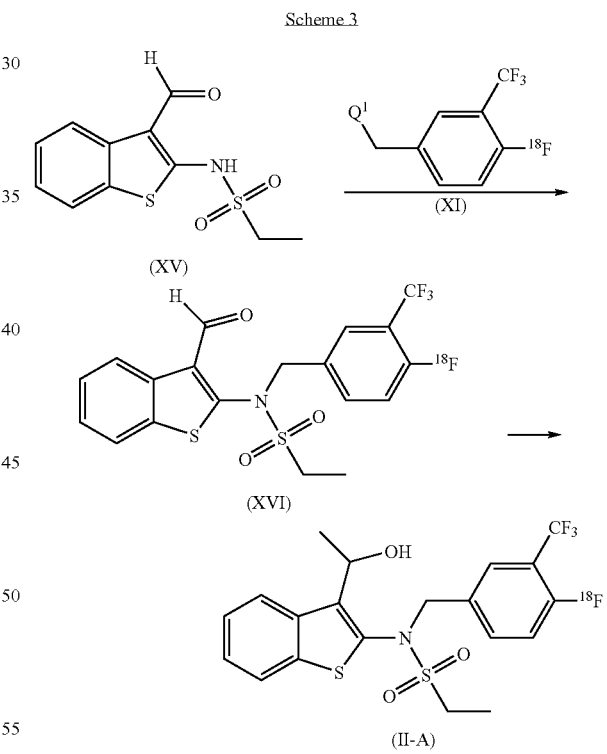

Accordingly, a suitably substituted compound of formula (XV), a known compound or compound prepared by known methods, is reacted with a suitably substituted radiolabelled compound of formula (XI), wherein $Q^1$ is a suitably selected leaving group, to yield the corresponding compound of formula (XVI).

For example, wherein $Q^1$ is a leaving group such as Br, Cl, I, and the like, preferably Br, the compound of formula (XV) is reacted with the compound of formula (XI), wherein the compound of formula (XI) is reacted with a compound of Accordingly, a suitably substituted compound of formula (X) wherein $A^1$ is $C_{1-4}$alkyl, preferably methyl, a known compound or compound prepared by known methods, is formula (XV), wherein the compound of formula (XV) is present in a molar excess; in the presence of an inorganic base such as NaH, Cs₂CO₃, K₂CO₃, and the like, preferably NaH; in an organic solvent such as DMF, THF, 1,4-dioxane, DMSO, and the like; preferably at a temperature in the range of from about 25° C. to about 100° C.; to yield the corresponding compound of formula (XVI).

Alternatively, wherein the compound of formula (XI), Q¹ is a leaving group such as OH, the compound of formula (XV) is reacted with the compound of formula (XI), under Mitsunobu conditions (in the presence of triphenylphosphine, and the like, in the presence of a coupling agent such as DEAD, and the like, in an organic solvent such as THF, and the like), to yield the corresponding compound of formula (XVI).

The compound of formula (XVI) is reacted with suitably selected organolmetallic reagent such as methyl magnesium bromide, methyllithium, and the like, preferably CH₃MgBr; wherein the organometallic reagent is preferably present in an amount of at least about 1 molar equivalent; in an organic solvent such as THF, 1,4-dioxane, and the like; preferably at a temperature in the range of from about –20° C. to about 25° C.; to yield the corresponding compound of formula (II-A).

The compound of formula (II-B) may be prepared according to the process outlined in Scheme 4.

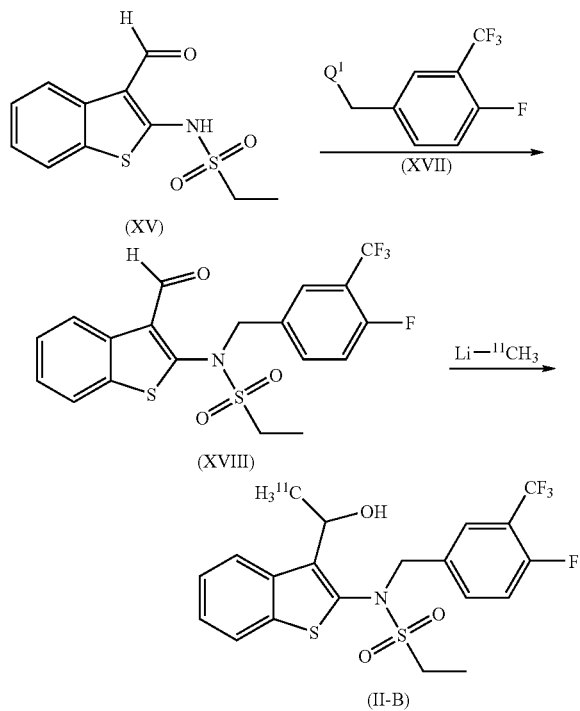

Accordingly, a suitably substituted compound of formula (XV), a known compound or compound prepared by known methods, is reacted with a suitably substituted compound of formula (XVII), wherein Q¹ is a suitably selected leaving group, to yield the corresponding compound of formula (XVIII).

For example, wherein Q¹ is a leaving group such as Br, Cl, I, and the like, preferably Br, the compound of formula (XV) is reacted with the compound of formula (XVII), wherein the compound of formula (XVII) is preferably present in an amount of at least one molar equivalent (relative to the moles of the compound of formula (XV); in the presence of an inorganic base such as NaH, Cs₂CO₃, K₂CO₃, and the like, preferably NaH; in an organic solvent such as DMF, THF, 1,4-dioxane, DMSO, and the like; preferably at a temperature in the range of from about 25° C. to about 100° C.; to yield the corresponding compound of formula (XVIII).

Alternatively, wherein the compound of formula (XI), Q¹ is a leaving group such as OH, the compound of formula (XV) is reacted with the compound of formula (XVII), under Mitsunobu conditions (in the presence of triphenylphosphine, and the like, in the presence of a coupling agent such as DEAD, and the like, in an organic solvent such as THF, and the like), to yield the corresponding compound of formula (XVIII).

A molar excess of the compound of formula (XVIII) is reacted with radiolabelled [¹¹C]methyllithium, a known compound or compound prepared by known methods; in an organic solvent such as THF, 1,4-dioxane, and the like, preferably THF; preferably at a temperature in the range of from about –20° C. to about 25° C.; to yield the corresponding compound of formula (II-B).

The radiolabelled compound of formula (XI) may be prepared according as outlined in Scheme 5.

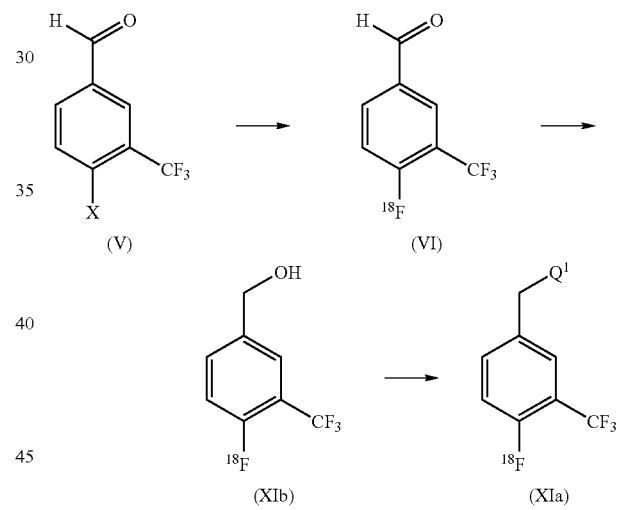

Accordingly, a compound of formula (V), wherein X is selected from the group consisting of N⁺(CH₃)₃, NO₂, Br and Cl; a known compound or compound prepared by known methods, is reacted with radiolabelled ¹⁸F⁻, a known compound or compound prepared by known methods; in the presence of a crown ether such as 18-crown-6 and the like or a cryptand such as KRYPTOFIX® 2.2.2, and the like; wherein the compound of formula (V) is preferably present in a molar excess of greater than about 100 times; in an organic solvent such as DMSO, DMF, CH₃CN, and the like, preferably DMSO; to yield the corresponding radiolabelled compound of formula (VI).

The compound of formula (VI) is reduced by reacting with a suitably selected reducing agent such as sodium borohydride, and the like; in a solvent such as water, and the like; to yield the corresponding compound of formula (XIb), a compound of formula (XI), wherein Q¹ is hydroxy.

The compound of formula (XIb) is then reacted with a suitably selected halogenating reagent such as PCl₃, PBr₃, PI$_3$, Ph$_3$PBr$_2$, Ph$_3$PI$_2$, P$_2$I$_4$; and the like, preferably Ph$_3$PBr$_2$; in an organic solvent such as DCM, DCE, chloroform, and the like, preferably DCM; to yield the corresponding compound of formula (XIa), a compound of formula (XI) wherein Q$^1$ is the corresponding halogen, such as Cl, Br, I, and the like. Preferably, the compound of formula (XIb) is reacted with a suitably selected brominating agent, to yield the corresponding compound of formula (XIa), wherein Q$^1$ is Br.

Compounds of formula (A) wherein the carbon atom of the methyl group bound at the 3-position of the benzothienyl group on the compound of formula (A) is replaced with $^{11}$C may be prepared by reacting a compound of formula (P1)

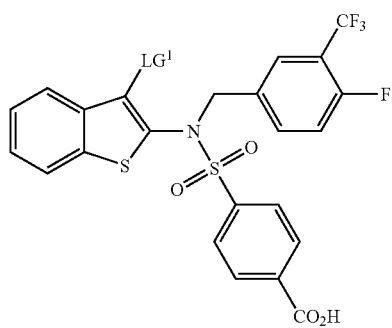

(P1)

wherein LG$^1$ is a suitably selected leaving group such as Br, I, and the like, is reacted with a radiolabelled $^{11}$CH$_3$-tin reagent such as 5-[$^{11}$C]methyl-1-aza-5-stanna-bicyclo[3.3.3]undecane (T. Forngren, L. Samuelsson, B. Langstrom J. Labelled Compd. Radiopharm. 2004, 47, 71-78), and the like; in the presence of a Pd(0) or Pd(II) species such as Pd(allyl-chloride)$_2$, PdCl$_2$(CH$_3$CN)$_2$, or Pd$_2$(dba)$_3$ with AsPh$_3$, and the like; in an organic solvent such as DMF, and the like; preferably for about 2 to about 10 minutes; preferably at about 100° C.

Compounds of formula (A) wherein the carbon atom of the carboxy group, bound at the 4-position of the phenyl-sulfonyl-group on the compound of formula (A) is replaced with $^{11}$C may be prepared by reacting a compound of formula (P2)

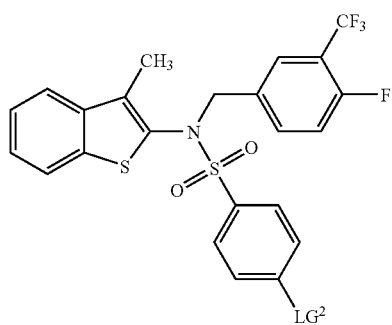

(P2)

wherein LG$^2$ is a suitably selected leaving group such as Br, I, and the like, with a suitably selected organometallic reagent such as, n-butyl lithium, and the like; and then trapped with radiolabelled $^{11}$CO$_2$, in an organic solvent such as THF, and the like; under an inert atmosphere.

Compounds of formula (B) wherein the terminal carbon atom on the ethylsulfonyl-portion of the compound of formula (B) is replaced with $^{11}$C may be prepared by reacting a compound of formula (P3)

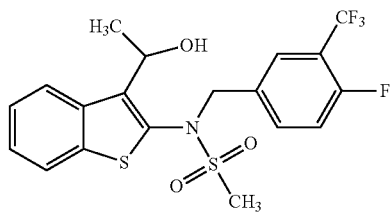

(P3)

with greater than about 2 equivalents of a suitably selected organometallic reagent or lithium amide base, such as, lithium diisopropylamide, and the like; in an organic solvent such as THF, and the like; under an inert atmosphere. The resulting lithio species is then treated with [$^{11}$C]methyl iodide according to known methods to yield the desired [$^{11}$C]-labeled compound (B).

For use in medicine, salts of the compounds of the present invention refer to non-toxic "pharmaceutically acceptable salts." Other salts may, however, be useful in the preparation of the compounds of the present invention or of their pharmaceutically acceptable salts thereof. Suitable pharmaceutically acceptable salts of the compounds of the present invention include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the present invention carry an acidic moiety, suitable pharmaceutically acceptable salts thereof may include alkali metal salts, such as sodium or potassium salts; alkaline earth metal salts, such as calcium or magnesium salts; and salts formed with suitable organic ligands, such as quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2- sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholin, piperazine, potassium hydroxide, 1-(2-hydroxyethyl)-pyrrolidine, secondary amine, sodium hydroxide, triethanolamine, tromethamine and zinc hydroxide.

Some of the compounds of the present invention may form "solvates" with water (i.e., hydrates) or common organic solvents, and such solvates are also intended to be encompassed within the scope of this invention. The skilled artisan will understand that the term compound as used herein, is meant to include solvated compounds of the present invention.

Embodiments of the present invention include prodrugs of the compounds of the present invention. In general, such "prodrugs" will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

As used herein, unless otherwise noted, the term "isolated form" shall mean that the compound is present in a form which is separate from any solid mixture with another compound(s), solvent system or biological environment. In an embodiment, the compound of formula (A) is present in an isolated form. In another embodiment, the compound of formula (B) is present in an isolated form. In an embodiment, the compound of formula (I) is present in an isolated form. In another embodiment, the compound of formula (II) is present in an isolated form.

As used herein, unless otherwise noted, the term "substantially pure compound" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment, the compound of formula (A) is present as a substantially pure form. In another embodiment, the compound of formula (B) is present as a substantially pure form. In an embodiment, the compound of formula (I) is present as a substantially pure form. In another embodiment, the compound of formula (II) is present as a substantially pure form.

As used herein, unless otherwise noted, the term "substantially free of a corresponding salt form(s)" shall mean that mole percent of the corresponding salt form(s) in the isolated compound is less than about 5 mole percent, preferably less than about 2 mole percent, more preferably, less than about 0.5 mole percent, most preferably less than about 0.1 mole percent. In an embodiment, the compound of formula (A) is present substantially free of corresponding form(s). In another embodiment, the compound of formula (B) is present as substantially free of corresponding form(s). In an embodiment, the compound of formula (I) is present substantially free of corresponding form(s). In another embodiment, the compound of formula (II) is present as substantially free of corresponding form(s).

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The compounds of the present invention are useful in PET imaging of the central and/or peripheral nervous system. As used herein, the term "central nervous system" includes, but is not limited to, the brain and spinal cord. Further, as used herein, the term "peripheral nervous system" includes, but is not limited to, the cranial nerves and the spinal nerves including their associated sensory receptors.

The present invention is further directed to pharmaceutical compositions containing any of the compounds described herein, with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for parenteral administration, the carrier will usually consist of sterile water and other ingredients may be added to increase solubility or preservation; and for injectable suspensions or solutions the carrier may include aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1 µg to about 1000 mg or any range therein, and may be given at a dosage of from about 0.1 µg to about 100 mg/kg/day, or any range therein, preferably from about 1.0 µg to about 50 mg/kg/day, or any range therein. The dosages, however, may be varied depending upon the requirement of the patients, the severity of the condition being treated and the compound being employed. The use of either daily administration or post-periodic dosing may be employed. Advantageously, compounds of the present invention may be administered in a single daily dose, or the total daily dosage may be administered in divided doses of two, three or four times daily.

Preferably the pharmaceutical compositions of the present invention are in unit dosage forms from such as sterile parenteral solutions or suspensions, metered aerosol or liquid sprays, drops, ampoules or autoinjector devices or suppositories. Alternatively, the composition may be presented in a form suitable for once-weekly or once-monthly administration.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods described in the present invention may also be carried out using a pharmaceutical composition comprising any of the compounds as defined herein and a pharmaceutically acceptable carrier. The pharmaceutical composition may contain between about 0.1 µg and about 1000 mg of the compound, or any range therein; preferably about 1.0 µg to about 100 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration may include liquid forms, such as solutions, syrups, elixers, emulsions, and suspensions. Forms useful for parenteral administration may include sterile solutions, emulsions and suspensions.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, any of the compound described herein, as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain. Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

The following Examples are set forth to aid in the understanding of the invention, and are not intended and should not be construed to limit in any way the invention set forth in the claims which follow thereafter. Further, one skilled in the art will recognize that Examples 1 and 2 describe the synthesis of non-radiolabelled compounds.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

N-[4-Fluoro-3-(trifluoromethyl)-benzyl]-N-(3-methylbenzo[b]thiophen-2-yl)-4-carboxy-benzenesulfonamide, sodium salt

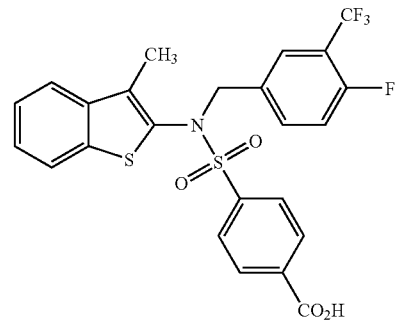

STEP A:
tert-Butyl-3-methylbenzo[b]thiophen-2-ylcarbamate

A 5-L 4-neck flask equipped with an overhead mechanical stirrer, $N_2$ inlet/outlet adapter, reflux condenser, heating mantle and thermocouple was charged with t-butyl alcohol (2.11 L), 3-methyl-benzo[b]thiophene-2-carboxylic acid (225.0 g, 1.17 mol), and diisopropylethylamine (225 mL, 1.29 mol). Diphenylphosphorylazide (304 mL, 1.4 mol) was premixed with toluene (300 mL) and then added drop-wise over 10 min. The resulting mixture was refluxed with stirring for 21 h, cooled to 22° C. and then evaporated in vacuo. The resulting residue was dissolved in $CH_2Cl_2$ (1 L), washed with 1 N NaOH (500 mL), brine (500 mL), the organic layer separated, dried over $MgSO_4$, filtered, and evaporated in vacuo to yield a dark orange oil (557 g). The oil was purified by the flash column chromatography ($SiO_2$) eluting with heptane-EtOAc to yield tert-butyl-3-methylbenzo[b]thiophen-2-ylcarbamate as a pale yellow solid. $^1$H-NMR (CDCl$_3$) δ 7.71

(d, 1H), 7.54 (d, 1H), 7.36-7.31 (m, 1H), 7.30-7.20 (m, 1H), 6.75 (br s, 1H), 2.23 (s, 3H), 1.55 (s, 9H).

STEP B: 3-Methylbenzo[b]thiophen-2-amine hydrochloride

A 5-L 3-neck flask equipped with an overhead mechanical stirrer, $N_2$ inlet/outlet adapter, and thermocouple was charged with 4M HCl in 1,4-dioxane (3.1 L), tert-butyl-3-methyl-benzo[b]thiophen-2-ylcarbamate (265 g, 1.0 mol) and stirred for 18 h at 22° C. The resulting white precipitate was collected by filtration, washed with diethyl ether (3×500 mL), and dried under house vacuum at 40° C. for 48 h to yield 3-methylbenzo[b]thiophen-2-amine hydrochloride as a white solid. $^1$H-NMR (DMSO-$d_6$) δ 8.7 (br s, 3H), 7.71 (d, 1H), 7.44 (d, 1H), 7.29 (t, 1H), 7.14 (t, 1H), 2.184 (s, 3H).

STEP C: N-(3-Methylbenzo[b]thiophen-2-yl)-4-carboxy-benzenesulfonamide

A 12-L 4-neck flask equipped with an overhead mechanical stirrer, $N_2$ inlet/outlet adapter, and thermocouple was charged with THF (3.26 L) and 3-methylbenzo[b]thiophen-2-amine hydrochloride (326 g, 1.6 mol) followed by pyridine (265 mL, 3.3 mol). The resulting mixture was cooled to 5° C. using a ice bath, to which was added a solution of 4-(chlorosulfonyl)benzoic acid (396 g, 1.8 mol) dissolved in THF (2.44 L), drop-wise. The resulting mixture was allowed to stir at ambient temperature for 72 h, was then diluted with EtOAc (4 L), washed with 1N HCl (1 L), brine (1 L), the organic layer dried over $Na_2SO_4$, filtered and evaporated under reduced pressure to yield a residue. The residue was purified by triturating with EtOAc/heptane (1:1/1 L). The resulting slurry was filtered, washed with heptane (2×250 mL) and dried in a vacuum oven at 40° C. for 18 h to yield N-(3-methylbenzo[b]thiophen-2-yl)-4-carboxy-benzenesulfonamide as a white solid. $^1$H-NMR (DMSO-$d_6$) δ13.51 (br s, 1H), 10.65 (br s, 1H), 8.12 (d, 2H), 7.86 (d, 2H), 7.83-7.79 (m, 1H), 7.66-7.63 (m, 1H), 7.37-7.33 (m, 1H), 2.03 (s, 3H).

STEP D: N-(3-Methylbenzo[b]thiophen-2-yl)-4-carbomethoxy-benzenesulfonamide

A 12-L 4-neck flask equipped with an overhead mechanical stirrer, $N_2$ inlet/outlet adapter, and thermocouple was charged with MeOH (7.5 L) and N-(3-methylbenzo[b]thiophen-2-yl)-4-carboxy-benzenesulfonamide (470 g, 1.35 mol). Sulfuric acid (24 mL, 0.45 mol) was added and the resulting mixture was then refluxed for 18 h. The resulting mixture was cooled, diluted with EtOAc (4 L), washed with 1N NaOH (2 L), and $H_2O$ (6 L). The aqueous layer with extracted with EtOAc (4×4 L), the combined organic extracts washed with brine (1 L), dried over $Na_2SO_4$, filtered and evaporated under reduced pressure to yield a red, thick oil. $^1$H-NMR (DMSO-$d_6$) δ 7.89 (d, 2H), 7.81 (d, 2H), 7.41 (d, 1H), 7.16 (d, 1H), 7.09-7.04 (m, 1H), 6.91-6.85 (m, 1H), 3.82 (s, 3H), 1.99 (s, 3H).

A 5-L 3-neck flask equipped with an overhead mechanical stirrer, $N_2$ inlet/outlet adapter, and thermocouple was charged with the red, thick oil prepared above in $H_2O$ (4 L). The resulting solution was acidified with 1N HCl (200 mL) until pH=1 and the resulting mixture allowed to stir for 30 min at ambient temperature. The resulting solid was filtered, washed with $H_2O$ (2×250 mL) and dried in a vacuum oven at 50° C. for 72 h to yield N-(3-methylbenzo[b]thiophen-2-yl)-4-carbomethoxy-benzenesulfonamide as a white solid. $^1$H-NMR (DMSO-$d_6$) δ 10.67 (br s, 1H), 8.13 (d, 2H), 8.00 (d, 2H), 7.90-7.77 (m, 1H), 7.64-7.61 (m, 1H), 7.36-7.32 (m, 2H), 3.89 (s, 3H), 2.02 (s, 3H).

STEP E: N-[4-Fluoro-3-(trifluoromethyl)-benzyl]-N-(3-methylbenzo[b]thiophen-2-yl)-4-carbomethoxy-benzenesulfonamide A 12-L 4-neck flask equipped with an overhead mechanical stirrer, $N_2$ inlet/outlet adapter, and thermocouple was charged with DMF (4.9 L), N-(3-methylbenzo[b]thiophen-2-yl)-4-carbomethoxy-benzenesulfonamide (245 g, 0.68 mol) and $K_2CO_3$ (112 g, 0.81 mol). 4-Fluoro-3-(trifluoromethyl)benzyl bromide (210 mL, 0.81 mol) was then added dropwise over 15 min and the resulting mixture was stirred for 18 h at room temperature. The resulting mixture was poured into cold $H_2O$ (10 L), stirred for 30 min, to which was then added EtOAc (4 L). The layers were separated and the aqueous phase was extracted with EtOAc (2×1 L). The combined EtOAc layers were washed with brine (1 L), dried over $Na_2SO_4$, filtered and evaporated under reduced pressure to yield a residue. The residue was purified using flash column chromatography ($SiO_2$) eluting with heptane-EtOAc to yield N-[4-fluoro-3-(trifluoromethyl)-benzyl]-N-(3-methylbenzo[b]thiophen-2-yl)-4-carbomethoxy-benzenesulfonamide as a white solid. $^1$H-NMR (DMSO-$d_6$) δ 8.21 (d, 2H), 8.03 (d, 2H), 7.86-7.83 (m, 1H), 7.71-7.63 (m, 3H), 7.45-7.37 (m, 3H), 4.89 (br s, 2H), 3.93 (s, 3H), 1.94 (s, 3H).

STEP F: N-[4-Fluoro-3-(trifluoromethyl)-benzyl]-N-(3-methylbenzo[b]thiophen-2-yl)-4-carboxy-benzenesulfonamide A 3-L 4-neck flask equipped with an overhead mechanical stirrer, $N_2$ inlet/outlet adapter, condenser and thermocouple was charged with MeOH (1.9 L) and N-[4-fluoro-3-(trifluoromethyl)-benzyl]-N-(3-methylbenzo[b]thiophen-2-yl)-4-carbomethoxy-benzenesulfonamide (190 g, 0.35 mol) followed by 3M NaOH (412 mL, 1.2 mol) and the resulting mixture refluxed for 2 h. The resulting mixture was then cooled to room temperature, diluted with EtOAc (2 L) and 1N HCl (2 L), the layers separated and the aqueous phase extracted with EtOAc (2 L). The organic extracts were combined, washed with brine (1.5 L), dried over $Na_2SO_4$, filtered and evaporated under reduced pressure to yield a yellow solid. The yellow solid was placed in vacuum oven for 18 h at 50° C. to yield N-[4-fluoro-3-(trifluoromethyl)-benzyl]-N-(3-methylbenzo[b]thiophen-2-yl)-4-carboxy-benzenesulfonamide as a yellow solid. $^1$H-NMR (DMSO-$d_6$) δ 13.63 (s, 1H), 8.19 (d, 2H), 8.01 (d, 2H), 7.86-7.83 (m, 1H), 7.71-7.63 (m, 3H), 7.49-7.37 (M, 3H), 4.89 (br s, 1H), 1.95 (s, 3H).

EXAMPLE 2 (II)

N-(4-Fluoro-3-trifluoromethyl-benzyl)-N-[3-(1-hydroxy-ethyl)-benzo[b]thiophen-2-yl]-ethanesulfonamide

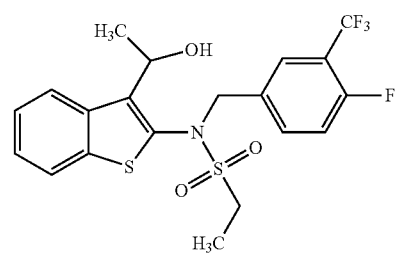

STEP A: Ethanesulfonic acid benzo[b]thiophen-2-ylamide

Ethanesulfonic acid benzo[b]thiophen-2-ylamide was prepared by reacting benzo[b]thiophen-2-ylamine and 4-ethanesulfonyl chloride, according to the procedure as described in Example 1, STEP C above.

STEP B: N-(3-Acetyl-benzo[b]thiophen-2-yl)-ethanesulfonamide

Tin (IV) chloride (173 µL, 1.48 mmol) was added to a solution of acetyl chloride (124 µL, 1.75 mmol) in dichloromethane (10 mL), at 0° C., and the resulting solution was stirred for 5 min. To the resulting mixture was then added a solution of ethanesulfonic acid benzo[b]thiophen-2-ylamide (325 mg, 1.35 mmol) in dichloromethane (2 mL) at 0° C. The resulting solution was allowed to warm to ambient temperature and then stirred overnight. The resulting solution was treated with water (10 mL), the organic layer separated, dried over sodium sulfate, filtered, and the solvent evaporated in vacuo to yield N-(3-acetyl-benzo[b]thiophen-2-yl)-ethanesulfonamide as a colorless solid. $^1$H-NMR (DMSO-$d_6$): δ 1.25 (t, 3H), 2.71 (s, 3H), 3.39 (q, 2H), 7.34-7.48 (m, 2H), 7.94 (d, 1H), 8.10 (d, 1H); MS: m/z 284.1 (MH$^+$).

STEP C: N-(3-Acetyl-benzo[b]thiophen-2-yl)-N-(4-fluoro-3-trifluoromethyl-benzyl)-ethanesulfonamide Sodium hydride (60% in oil, 46 mg, 1.15 mmol) was added to a solution of N-(3-acetyl-benzo[b]thiophen-2-yl)-ethanesulfonamide (310 mg, 1.09 mmol) in DMF (4 mL), at 0° C. The resulting mixture was stirred at 0° C. for 15 min, to which was added 4-fluoro-3-trifluoromethylbenzyl bromide (253 µL, 1.33 mmol) and the resulting mixture stirred at ambient temperature for 2 h. 15-Crown-5 ether (220 µL, 1.33 mmol) and an additional equivalent of 4-fluoro-3-trifluoromethylbenzyl bromide was then added. The resulting solution was stirred at ambient temperature overnight, water was then added, and the desired product extracted into ethyl acetate. The organic phase was washed with water (3×), brine, dried over sodium sulfate, filtered, and the solvent evaporated in vacuo to yield a residue. The residue was purified by flash column chromatography (SiO$_2$), eluting with an ethyl acetate-heptane gradient to yield N-(3-acetyl-benzo[b]thiophen-2-yl)-N-(4-fluoro-3-trifluoromethyl-benzyl)-ethanesulfonamide as an off-white solid. $^1$H-NMR (DMSO-$d_6$): δ 1.32 (t, 3H), 2.29 (s, 3H), 3.49 (q, 2H), 5.08 (s, 2H), 7.41-7.52 9m, 3H), 7.70-7.77 (m, 2H), 7.93-8.03 (m, 2H); MS: m/z 460.2 (MH$^+$).

STEP D: N-(4-Fluoro-3-trifluoromethyl-benzyl)-N-[3-(1-hydroxy-ethyl)-benzo[b]thiophen-2-yl]-ethanesulfonamide Sodium borohydride (0.14 g, 3.7 mmol) was added to a solution of N-(3-acetyl-benzo[b]thiophen-2-yl)-N-(4-fluoro-3-trifluoromethyl-benzyl)-ethanesulfonamide (0.268 g, 0.582 mmol) in ethanol (10 mL), and the resulting mixture was stirred at room temperature for 3 h. The solvent was evaporated, the residue partitioned between dichloromethane and water, the organic layer separated, dried over sodium sulfate, filtered, and the solvent evaporated in vacuo to yield a residue. The residue was purified by flash column chromatography (SiO$_2$), eluting with an ethyl acetate-heptane (10-40%) gradient to yield N-(4-fluoro-3-trifluoromethyl-benzyl)-N-[3-(1-hydroxy-ethyl)-benzo[b]thiophen-2-yl]-ethanesulfonamide as a colorless solid.
$^1$H-NMR (CDCl$_3$): δ 1.08 (br s, 3H), 1.50 (t, 3H), 3.27 (q, 2H), 4.42 (d, 1H), 4.94 (q, 1H), 5.29 (d, 1H), 7.13 (t, 1H), 7.35-7.40 (m, 2H), 7.49-7.54 (m, 2H), 7.58 (d, 1H), 7.74-7.77 (m, 1H), 8.12 (br d, 1H); MS: m/z 444.1 (M-OH)$^+$, 484.2 (MNa$^+$)

EXAMPLE 3

Liquid Formulation—Prophetic Example

As a specific embodiment of a pharmaceutical composition, a compound of formula (I) or a compound of formula (II), in an amount sufficient to yield about 20 mCi, is formulated according to known methods with a mixture of sterile saline and about 5% ethanol.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A radiolabelled compound selected from the group consisting of a compound of formula (A)

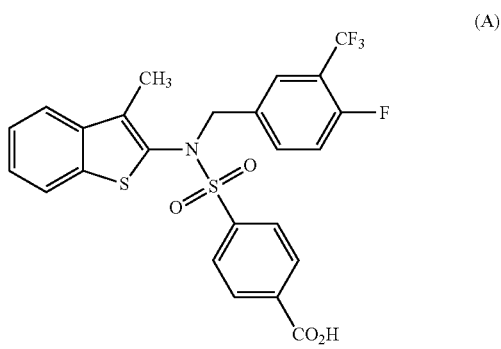

(A)

or pharmaceutically acceptable salt thereof; wherein one or more of the C and/or F atoms on the compound of formula (A) is replaced with the corresponding $^{11}$C or $^{18}$F;

and a compound of formula (B)

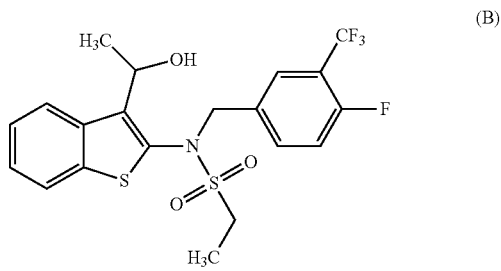

(B)

or pharmaceutically acceptable salt thereof; wherein one or more of the C and/or F atoms on the compound of formula (B) is replaced with the corresponding $^{11}$C or 18F.

2. A compound selected from the group consisting of
(a) a compound of formula (I)

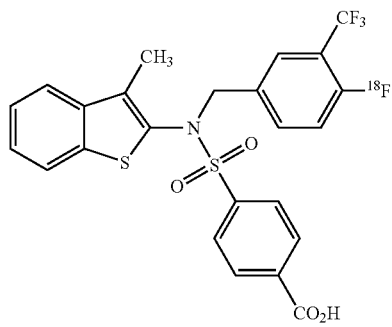

or pharmaceutically acceptable salt thereof;
(b) a compound of formula (II-A)

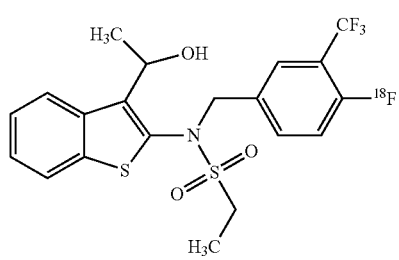

or pharmaceutically acceptable salt thereof; and
(c) a compound of formula (II-B)

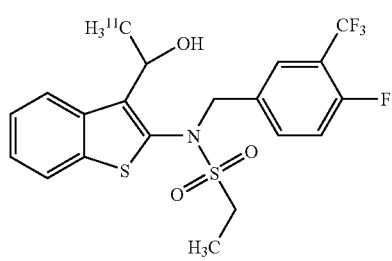

or pharmaceutically acceptable salt thereof.

3. A compound of formula (I)

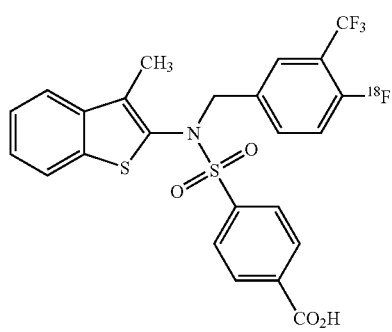

or pharmaceutically acceptable salt thereof.

4. A compound of formula (II-A)

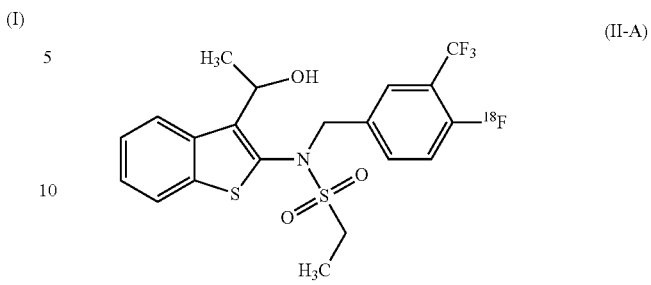

or pharmaceutically acceptable salt thereof.

5. A compound of formula (II-B)

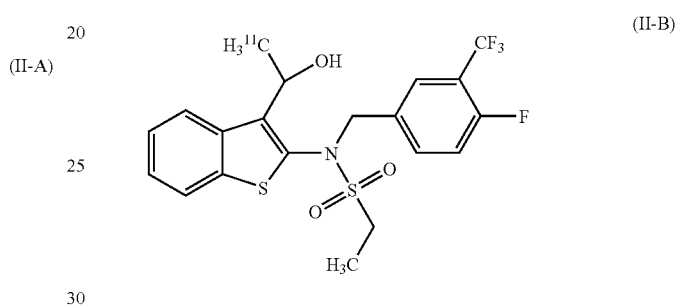

or pharmaceutically acceptable salt thereof.

6. A radiopharmaceutical composition which comprises a compound as in claim 2 and a pharmaceutically acceptable carrier or excipient.

7. A method for imaging of TRP M8 receptors in a mammal comprising administering to a mammal in need of such imaging an effective amount of a compound as in claim 2, and obtaining an image of TRP M8 receptors using positron emission tomography.

8. The method of claim 7, wherein the mammal is a human.

9. A method for imaging of the central or peripheral nervous system in a mammal comprising administering to a mammal in need of such imaging an effective amount of the compound as in claim 1, and obtaining an image of the central or peripheral nervous system in the mammal using positron emission tomography.

10. The method of claim 9, wherein the mammal is a human.

11. A method as in claim 9, wherein the central or peripheral nervous system being imaged is the brain or spinal cord.

12. A method for imaging of tissues bearing TRP M8 receptors in a mammal comprising administering to a mammal in need of such imaging an effective amount of a compound as in claim 2, and obtaining an image of the tissues using positron emission tomography.

13. The method of claim 12, wherein the mammal is a human.

14. A method for detection or quantification of TRP M8 receptors in mammalian tissue comprising contacting mammal tissue in which such detection or quantification is desired with an effective amount of a compound as in claim 1, and detecting or quantifying the TRP M8 receptors using positron emission tomography.

15. The method of claim 14, wherein the mammalian tissue is human tissue.

16. A process for the preparation of a compound of formula (I)

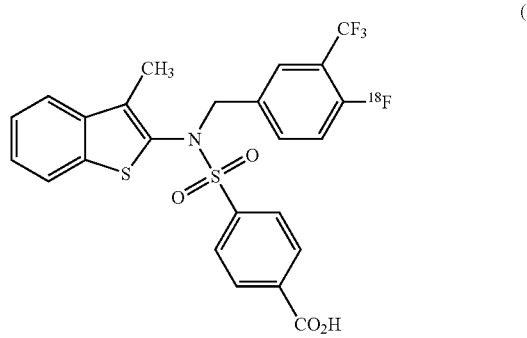

or pharmaceutically acceptable salt thereof; comprising

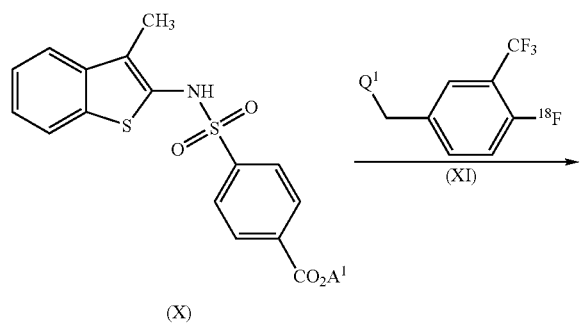

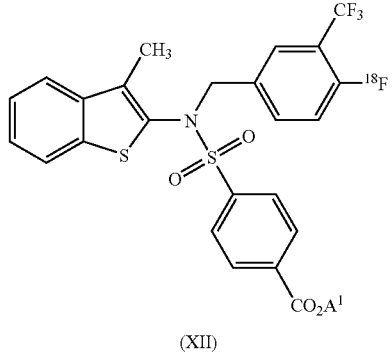

reacting a compound of formula (X), wherein $A^1$ is $C_{1-4}$alkyl with a radiolabelled compound of formula (XI), wherein $Q^1$ is a leaving group selected from the group consisting of Br, Cl, I, mesylate, and tosylate, to yield the corresponding compound of formula (XII);

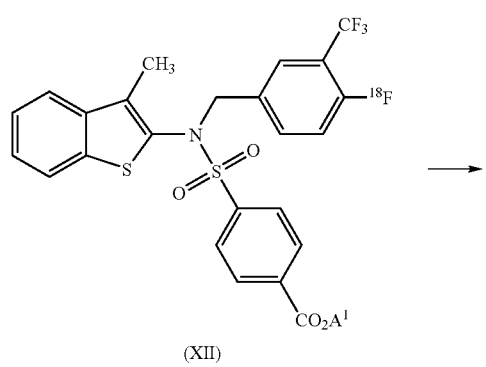

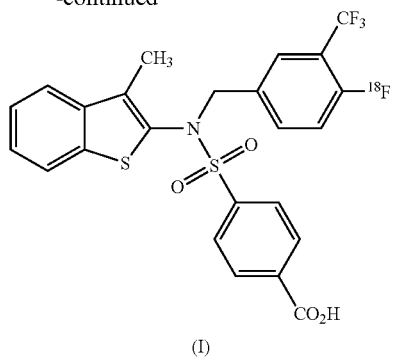

reacting the compound of formula (XII) with a base selected from the group consisting of NaH, $Cs_2CO_3$, and $K_2CO_3$; in an organic solvent selected from the group consisting of DMF, THF, 1,4-dioxane, DMSO, or mixture of said organic solvent and water; to yield the corresponding compound of formula (I).

17. A process for the preparation of a compound of formula (I)

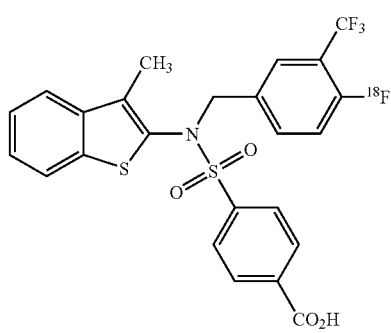

or pharmaceutically acceptable salt thereof; comprising

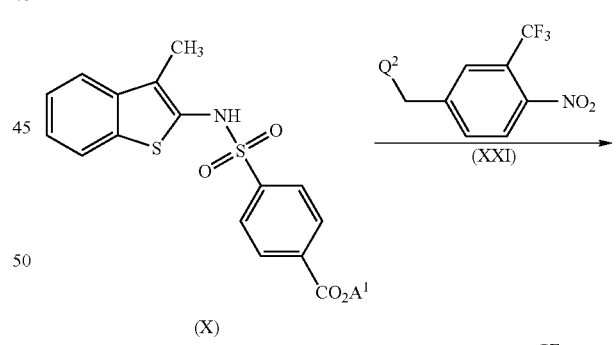

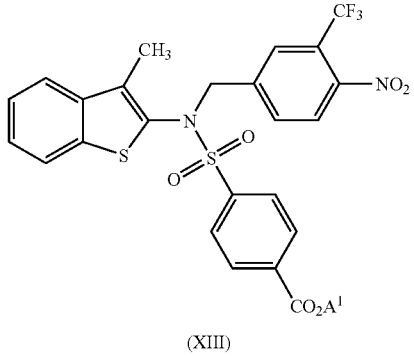

reacting a compound of formula (X) wherein $A^1$ is $C_{1-4}$alkyl, with a radiolabelled compound of formula (XXI), wherein $Q^2$ is a leaving group selected from the group consisting of Br, Cl, and I; in the presence of an inorganic base selected from the group consisting of NaH, $Cs_2CO_3$, and $K_2CO_3$; in an organic solvent selected from the group consisting of DMF, THF, 1,4-dioxane, and DMSO; to yield the corresponding compound of formula (XIII);

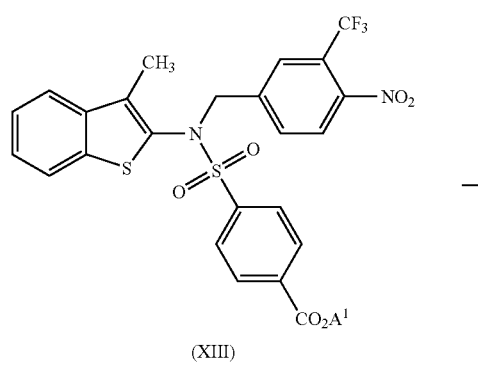

(XIII)

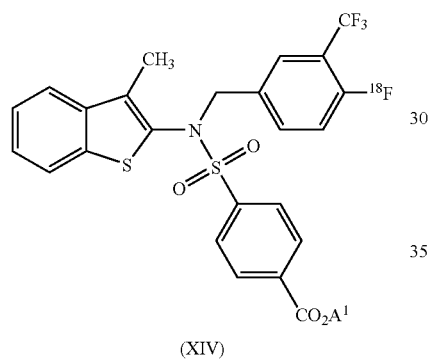

(XIV)

reacting the compound of formula (XIII) with radiolabelled $^{18}F^-$; in the presence of crown ether selected from the group consisting of 12-crown-4, 15-crown-5, 18-crown-6, dibenzo-18-crown-6, diaza-18-crown-6; or a cryptand which is KRYPTOFIX® 2.2.2; in an organic solvent selected from the group consisting of THF, DMF, DHF, $CH_3CN$, 1-4 dioxane and DMSO; to yield the corresponding radiolabelled compound of formula (XIV);

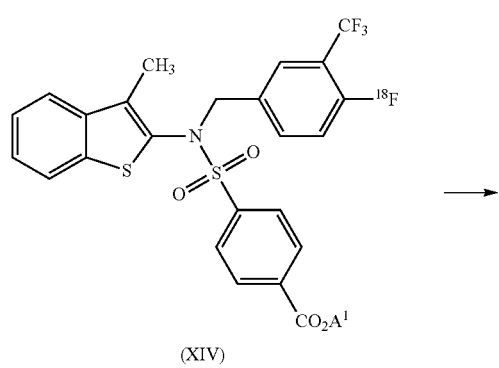

(XIV)

-continued

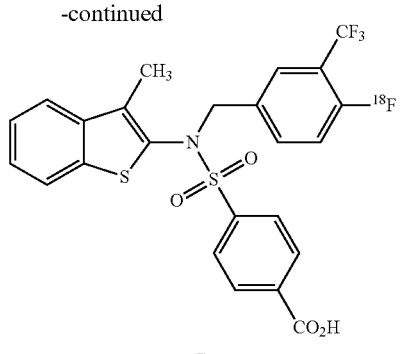

(I)

reacting the compound of formula (XIV) with a base selected from the group consisting of NaOH and LiOH; in an organic solvent or mixture of organic solvent and water selected from the group consisting of methanol, ethanol, and methanol/water, to yield the corresponding compound of formula (I).

18. A process for the preparation of a compound of formula (II-A)

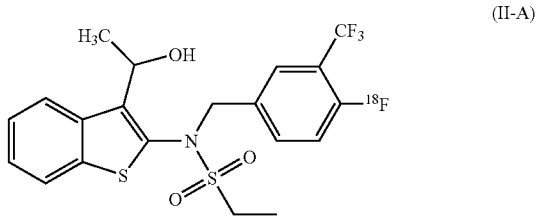

(II-A)

or pharmaceutically acceptable salt thereof; comprising

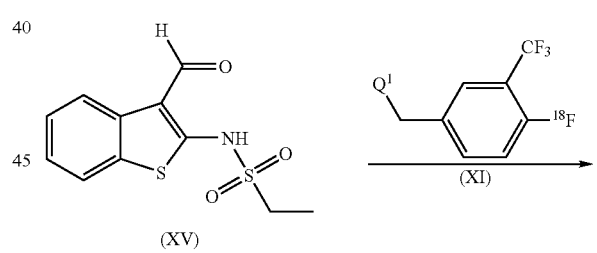

(XV) (XI)

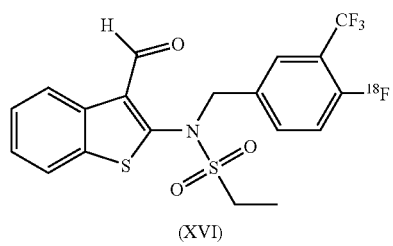

(XVI)

reacting a compound of formula (XV) with a radiolabelled compound of formula (XI), wherein $Q^1$ is a leaving group selected from the group consisting of Br, Cl, I, mesylate, and tosylate, to yield the corresponding compound of formula (XVI);

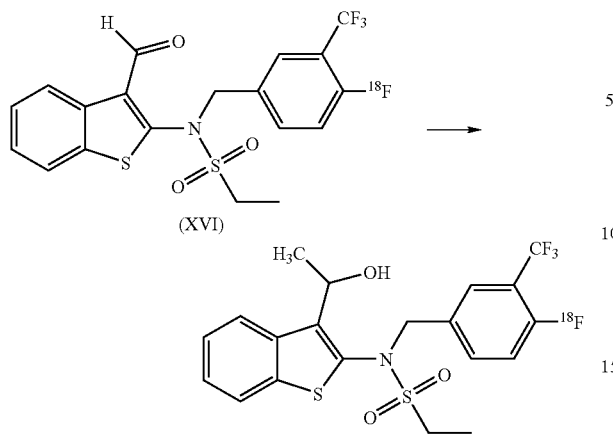

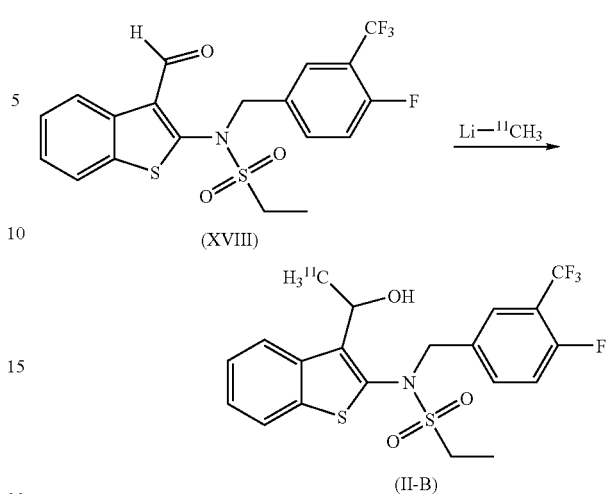

reacting the compound of formula (XVI) with an organometallic reagent selected from the group consisting of methyl magnesium bromide, and methyllithium; in an organic solvent selected from the group consisting of THF, DMF, DHF, CH$_3$CN, 1-4 dioxane and DMSO; to yield the corresponding compound of formula (II-A).

19. A process for the preparation of a compound of formula (II-B)

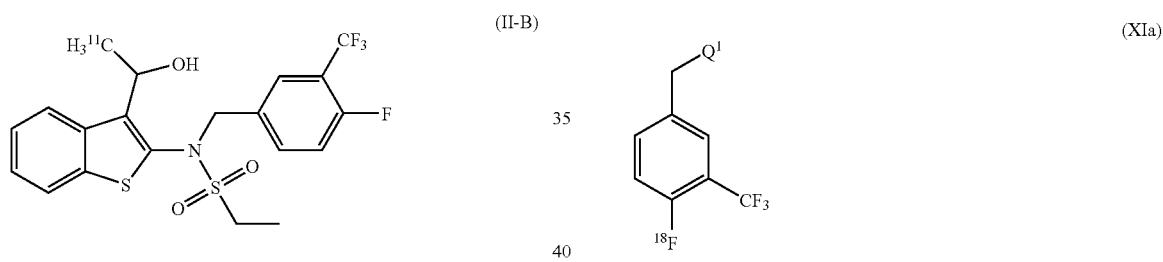

or pharmaceutically acceptable salt thereof; comprising

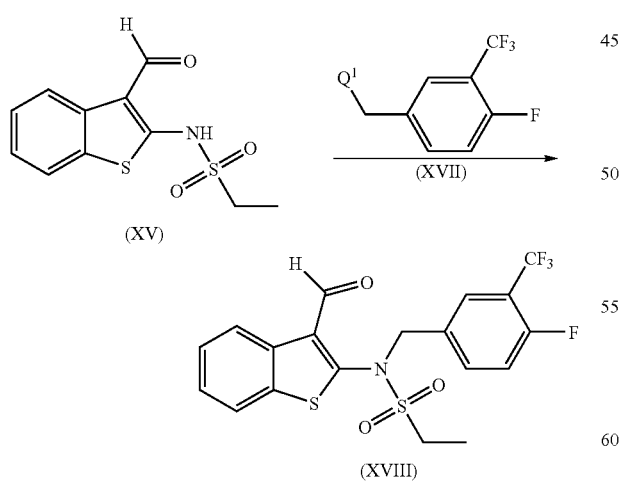

reacting a compound of formula (XV), wherein Q$^1$ is a leaving group selected from the group consisting of Br, Cl, I, mesylate, and tosylate, to yield the corresponding compound of formula (XVIII);

reacting a molar excess of the compound of formula (XVIII) with radiolabelled [$^{11}$C]methyllithium; in an organic solvent selected from the group consisting of THF, DMF, DHF, CH$_3$CN, 1-4 dioxane and DMSO; to yield the corresponding compound of formula (II-B).

20. A process for the preparation of a compound of formula (XIa)

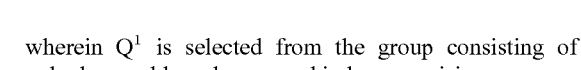

wherein Q$^1$ is selected from the group consisting of hydroxy, chloro, bromo and iodo; comprising

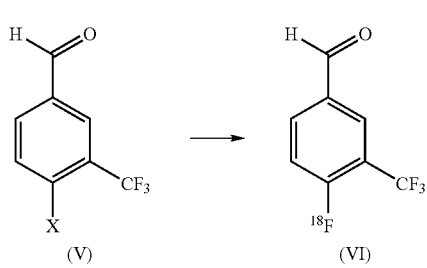

reacting a compound of formula (V), wherein X is selected from the group consisting of N$^+$(CH$_3$)$_3$, NO$_2$, Br and Cl; with radiolabelled $^{18}$F$^-$; in the presence of crown ether selected from the group consisting of 12-crown-4, 15-crown-5, 18-crown-6, dibenzo-18-crown-6, diaza-18-crown-6; or a cryptand which is KRYPTOFIX® 2.2.2; in an organic solvent selected from the group consisting of THF, DMF, DHF, CH$_3$CN, 1-4 dioxane and DMSO; to yield the corresponding radiolabelled compound of formula (VI);

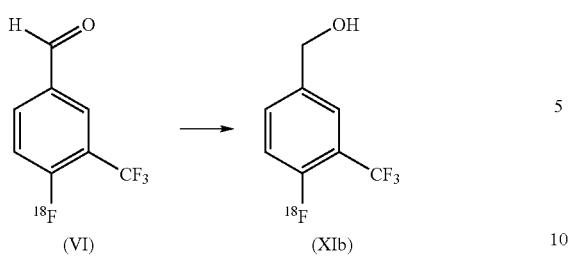

reacting the compound of formula (VI) with a reducing agent; in water; to yield the corresponding compound of formula (XIb), a compound of formula (XI), wherein $Q^1$ is hydroxy;

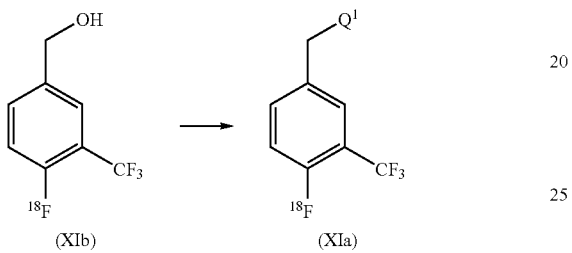

optionally reacting the compound of formula (XIb) with a chlorinating, brominating or iodinating reagent; to yield the corresponding compound of formula (XIa), a compound of formula (XI) wherein $Q^1$ is the corresponding chloro, bromo or iodo, respectively.

21. A process for the preparation of a compound of formula (A-1)

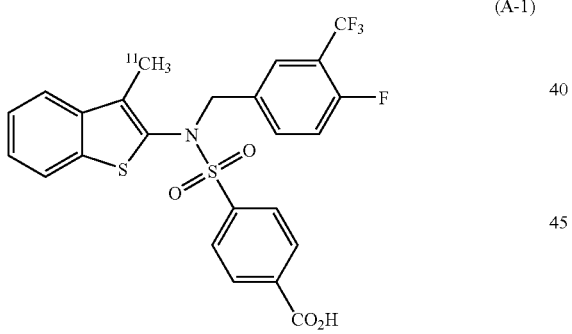

or pharmaceutically acceptable salt thereof; comprising

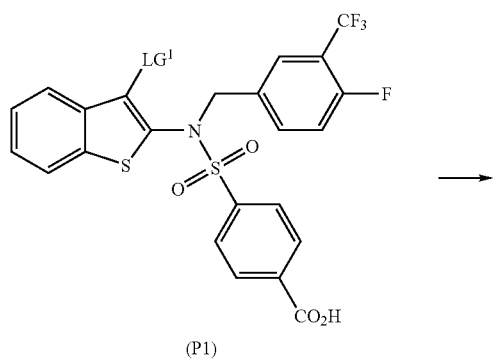

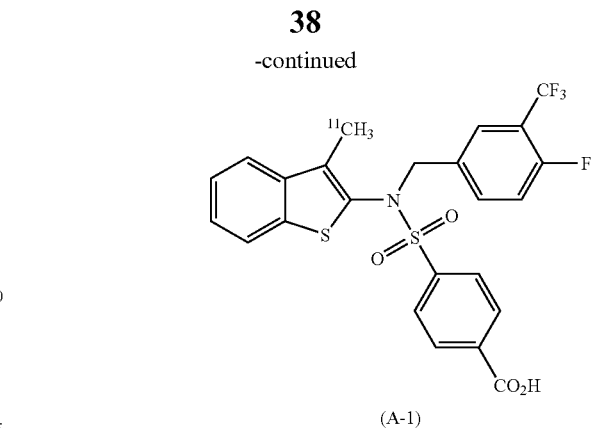

reacting a compound of formula (P1) wherein $LG^1$ is a leaving group selected from the group consisting of Br, Cl, and I; with a radiolabelled $^{11}CH_3$-tin reagent; in the presence of a Pd(0) or Pd(II) species; in an organic solvent selected from the group consisting of THF, DMF, DHF, $CH_3CN$, 1-4 dioxane and DMSO; to yield the corresponding compound of formula (A-1).

22. A process for the preparation of a compound of formula (A-2)

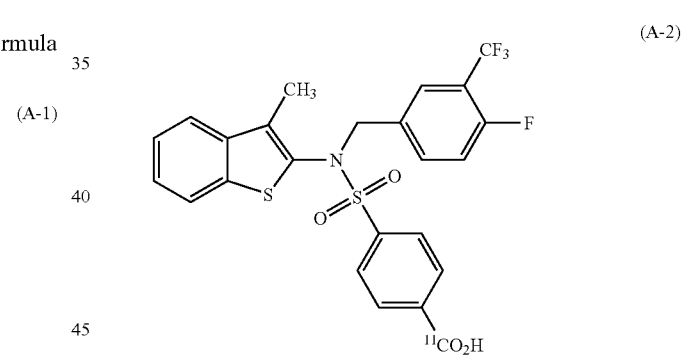

or pharmaceutically acceptable salt thereof; comprising

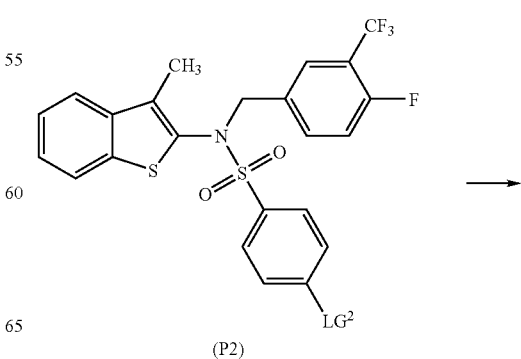

-continued

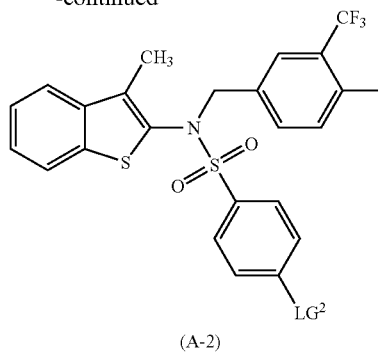

(A-2)

reacting a compound of formula (P2) wherein $LG^2$ is a leaving group; with an organometallic reagent selected from the group consisting of methyl magnesium bromide, and methyllithium; and then trapping with radiolabelled $^{11}CO_2$; in organic solvent selected from the group consisting of THF, DMF, DHF, $CH_3CN$, 1-4 dioxane and DMSO; to yield the corresponding compound of formula (A-2).

23. A process for the preparation of a compound of formula (B-1)

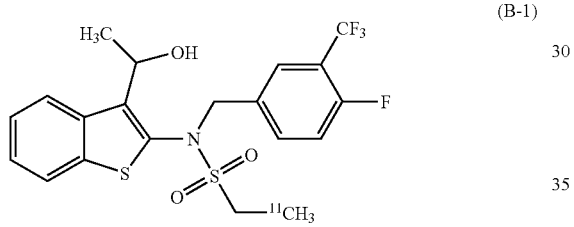

(B-1)

or pharmaceutically acceptable salt thereof; comprising

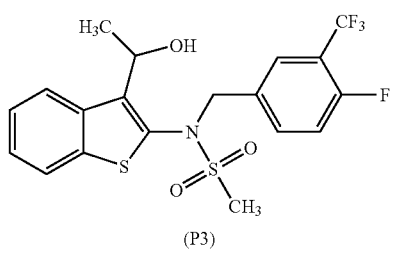

(P3)

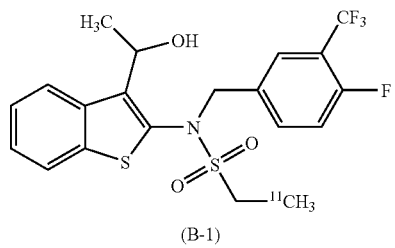

(B-1)

reacting a compound of formula (P3) with at least 2 equivalents of an organometallic reagent selected from the group consisting of methyl magnesium bromide, and methyllithium; or lithium amide base; organic solvent selected from the group consisting of THF, DMF, DHF, $CH_3CN$, 1-4 dioxane and DMSO; such; under an inert atmosphere; and then reacting with [$^{11}C$]methyl iodide; to yield the corresponding compound of formula (B-1).

* * * * *